(12) United States Patent
Duval (10) Patent No.: US 11,576,579 B2
(45) Date of Patent: Feb. 14, 2023

(54) MULTICHANNEL REFLECTIVE OPTICAL MEDICAL SENSOR DEVICE

(71) Applicant: Boston Scientific Scimed, Inc., Maple Grove, MN (US)

(72) Inventor: George Wilfred Duval, Sudbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 163 days.

(21) Appl. No.: 16/004,661

(22) Filed: Jun. 11, 2018

(65) Prior Publication Data
US 2018/0353075 A1     Dec. 13, 2018

Related U.S. Application Data

(60) Provisional application No. 62/518,725, filed on Jun. 13, 2017.

(51) Int. Cl.
*A61B 5/00* (2006.01)
*A61B 5/0205* (2006.01)
(Continued)

(52) U.S. Cl.
CPC .......... *A61B 5/0059* (2013.01); *A61B 5/0205* (2013.01); *A61B 5/0261* (2013.01);
(Continued)

(58) Field of Classification Search
CPC .............. A61B 5/0059; A61B 5/02416; A61B 5/14551; A61B 5/7207; A61B 5/721;
(Continued)

(56) References Cited

U.S. PATENT DOCUMENTS

| 6,018,673 A * | 1/2000 | Chin ................. A61B 5/14552 356/41 |
| 11,179,080 B2 | 11/2021 | Duval |

(Continued)

FOREIGN PATENT DOCUMENTS

| WO | 2013166465 | 11/2013 |
| WO | 2016086053 | 6/2016 |
| WO | 2018231672 | 12/2018 |

OTHER PUBLICATIONS

"Afe4405 Ultra-Small, Integrated AFE with FIFO for Wearable, Optical Heart-Rate Monitoring and Bio-Sensing," Texas Instruments Datasheet, Revised May 2016 (11 pages).
(Continued)

*Primary Examiner* — Devin B Henson
*Assistant Examiner* — Justin Xu
(74) *Attorney, Agent, or Firm* — Pauly, DeVries, Smith & Deffner LLC (57) ABSTRACT

Embodiments herein relate to reflective optical medical sensor devices. In an embodiment, a reflective optical medical sensor device including a central optical detector and a plurality of light emitter units disposed around the central optical detector is provided. A plurality of peripheral optical detectors can be disposed to the outside of the plurality of light emitter units. Each of the plurality of peripheral optical detectors can form a channel pair with one of the plurality of light emitter units. The reflective optical medical sensor device can also include a controller in electrical communication with the central optical detector, the light emitter units, and the peripheral optical detectors. The controller can be configured to measure performance of channel pairs; select a particular channel pair; and measure a physiological parameter using the selected channel pair. Other embodiments are also included herein.

20 Claims, 10 Drawing Sheets

(51) Int. Cl.
    *A61B 5/024*     (2006.01)
    *A61B 5/026*     (2006.01)
    *A61B 5/1455*     (2006.01)
    *G01J 3/10*     (2006.01)
    *G01J 3/28*     (2006.01)
    *G01J 3/08*     (2006.01)
    *G01J 3/42*     (2006.01)
    *A61B 5/021*     (2006.01)
    *A61B 5/08*     (2006.01)

(52) U.S. Cl.
CPC ...... *A61B 5/02416* (2013.01); *A61B 5/14551* (2013.01); *A61B 5/6823* (2013.01); *A61B 5/721* (2013.01); *A61B 5/7207* (2013.01); *G01J 3/10* (2013.01); *G01J 3/2803* (2013.01); *G01J 3/42* (2013.01); *A61B 5/021* (2013.01); *A61B 5/02433* (2013.01); *A61B 5/08* (2013.01); *A61B 5/0816* (2013.01); *A61B 5/14552* (2013.01); *A61B 2560/0204* (2013.01); *A61B 2560/0209* (2013.01); *A61B 2562/0219* (2013.01); *A61B 2562/0238* (2013.01); *A61B 2562/046* (2013.01); *A61B 2562/066* (2013.01); *A61B 2562/164* (2013.01)

(58) Field of Classification Search
CPC ... A61B 5/6823; A61B 5/0205; A61B 5/0261; A61B 5/08; A61B 2560/0204; A61B 2562/0219; A61B 2562/164; A61B 2560/0209; A61B 2562/066; A61B 2562/046; A61B 2562/0238; A61B 5/14552; A61B 5/0816; A61B 5/02433; A61B 5/021; G01J 3/42; G01J 3/2803; G01J 3/10
See application file for complete search history.

(56) References Cited

U.S. PATENT DOCUMENTS

| | | | |
|---|---|---|---|
| 2012/0209086 A1 | 8/2012 | Beute | |
| 2013/0041268 A1 | 2/2013 | Rimoldi et al. | |
| 2013/0324816 A1* | 12/2013 | Bechtel | A61B 90/11 600/331 |
| 2014/0012144 A1 | 1/2014 | Crone et al. | |
| 2014/0243632 A1 | 8/2014 | Ulrich et al. | |
| 2015/0374245 A1* | 12/2015 | Szilagyi | A61B 5/024 600/479 |
| 2016/0113530 A1* | 4/2016 | Nagahiro | A61B 5/0082 600/407 |
| 2016/0120444 A1 | 5/2016 | Hsu et al. | |
| 2017/0055907 A1* | 3/2017 | Altebaeumer | A61B 5/02416 |
| 2017/0127959 A1 | 5/2017 | Paulussen et al. | |
| 2018/0020960 A1* | 1/2018 | Sarussi | G01N 33/492 600/310 |
| 2019/0021637 A1 | 1/2019 | Duval et al. | |

OTHER PUBLICATIONS

Alzahrani, Abdullah et al., "A Multi-Channel Opto-Electronic Sensor to Accurately Monitor Heart Rate against Motion Artifacts during exercise," Sensors 2015, 15, 25681-25702 (22 pages).
"BPW 34 SR Version 1.3," Datasheet by OSRAM Opto Semiconductors, Mar. 31, 2016 (13 pages).
Chreiteh, Shadi S. et al., "A Clinical Study of Short-Term Sternal Photoplethysmography: Recordings from Patients with Obstructive Airways Diseases," Abstract Only 2016 38th Annual International Conference of the IEEE Engineering in Medicine and Biology Society (EMBC), 2016, pp. 2712-2716.(1 page).
Chreiteh, Shadi S. et al., "Long-Term Quasi-Continuous Oxygen Saturation Levels Obtained from Sternal Photoplethysmography on Patients with Obstructive Lung Diseases," Abstract Only 2016 38th Annual International Conference of the IEEE Engineering in Medicine and Biology Society (EMBC), 2016, pp. 2725-2728 (1 page).
Fontaine, Alexandra et al., "Reflectance Based Pulse Oximeter for the Chest and Wrist," Worcester Polytechnic Institute, 2013 (131 pages).
Friedland, Shai et al., "Reflectance Spectrophotometry for the assessment of mucosal perfusion in the gastrointestinal tract," Gastrointest Endoscopy Clin N Am 14(2004) 539-553 (15 pages).
Mendelson, Y. et al., "Noninvasive Pulse Oximetry Utilizing Skin Relectance Photoplethysmography," IEEE Transactions on Biomedical Engineering (1988): 35, 10, 798-805 (8 pages).
"New Sensor for Fitness Tracking in Smarwatches and Fitness Armbands," Press Release by OSRAM Opto Semiconductors, Nov. 8, 2015 (3 pages).
Scholbach, Thomas et al., "Dynamic Tissue Perfusion Measurement in the Intestinal Wall—Correlation with Ulcerative Colitis," J Med Ultrasound 2010;18(2):62-70 (9 pages).
Schreiner, Collin et al., "Blood Oxygen Level Measurement with a Chest-Based Pulse Oximetry Prototype System," Computing in Cardiology, 2010, pp. 537-540 (4 pages).
"SFH7060 Version 1.1," BioMon Sensor Datasheet by OSRAM Opto Semiconductors, Apr. 20, 2016 (24 pages).
Hashemi, Hooman "Transimpedance Amplifiers (TIA): Choosing the best Amplifier for the Job," Texas Instruments Application Report SNOA942A—Nov. 2015—Revised May 2017 (8 pages).
International Search Report and Written Opinion for International Application No. PCT/US2018/036823 dated Aug. 30, 2018 (14 pages).
International Preliminary Report on Patentability for PCT Application No. PCT/US2018/036823 dated Dec. 26, 2019 (10 pages).
Communication Pursuant to Article 94(3) EPC for European Patent Application No. 18737747.8 dated Dec. 18, 2020 (5 pages).
Non-Final Office Action for U.S. Appl. No. 16/041,915 dated Dec. 8, 2020 (22 pages).
Response to Communication Pursuant to Rules 161(1) and 162 EPC for European Patent Application No. 18737747.8 filed Aug. 3, 2020 (14 pages).
"Response to Communication Pursuant to Article 94(3) EPC," for European Patent Application No. 18737747.8 filed Apr. 27, 2021 (11 pages).
"Response to Non-Final Rejection," dated Dec. 8, 2020 for U.S. Appl. No. 16/041,915, submitted via EFS-Web on Apr. 1, 2021, 13 pages.
"Notice of Allowance," for U.S. Appl. No. 16/041,915 dated Jul. 27, 2021 (19 pages).

* cited by examiner

MULTICHANNEL REFLECTIVE OPTICAL MEDICAL SENSOR DEVICE

This application claims the benefit of U.S. Provisional Application No. 62/518,725, filed Jun. 13, 2017, the content of which is herein incorporated by reference in its entirety.

FIELD

Embodiments herein relate to reflective optical medical sensor devices and methods of using the same.

BACKGROUND

Photoplethysmography (PPG) is a minimally-invasive procedure used by medical professionals to monitor one or more physiological parameters of a patient using an optical sensor. PPG is frequently performed using a single optical sensor placed over the fingertip or earlobe of a patient.

Frequently, PPG makes uses of low-intensity infrared (IR) light. When light travels through biological tissues it is absorbed by bones, skin pigments and both venous and arterial blood. Since light is more strongly absorbed by blood than the surrounding tissues, the changes in blood flow can be detected by PPG sensors as changes in the intensity of light. The voltage signal from PPG can be proportional to the quantity of blood flowing through the blood vessels.

SUMMARY

Embodiments herein relate to reflective optical medical sensor devices. In a first aspect, a reflective optical medical sensor device is provided. The reflective optical medical sensor device can include a central optical detector and a plurality of light emitter units disposed around the central optical detector. Each of the plurality of light emitter units can be disposed a distance from the central optical detector. The reflective optical medical sensor device can also include a plurality of peripheral optical detectors disposed to the outside of the plurality of light emitter units. Each of the plurality of peripheral optical detectors can form a channel pair with one of the plurality of light emitter units. The reflective optical medical sensor device can also include a controller in electrical communication with the central optical detector, the plurality of light emitter units, and the plurality of peripheral optical detectors. The controller can be configured to measure performance of channel pairs; select a particular channel pair; and measure a physiological parameter using the selected channel pair.

In a second aspect, in addition to one or more of the preceding or following aspects, or in the alternative to some aspects, each of the plurality of light emitter units can include a first light emitter configured to emit light at a first wavelength max of peak emission, a second light emitter configured to emit light at a second wavelength of peak emission, and a third light emitter configured to emit light at a third wavelength of peak emission.

In a third aspect, in addition to one or more of the preceding or following aspects, or in the alternative to some aspects, the first wavelength of peak emission for the first light emitter is about 940 to 960 nm, the second wavelength of peak emission for the second light emitter is about 650 to 670 nm, and the third wavelength of peak emission for the third light emitter is about 520 to 540 nm.

In a fourth aspect, in addition to one or more of the preceding or following aspects, or in the alternative to some aspects, each of the light emitter units can be disposed a distance from the central optical detector of about 7 mm to about 11 mm.

In a fifth aspect, in addition to one or more of the preceding or following aspects, or in the alternative to some aspects, the light emitter unit and peripheral optical detector of each channel pair is disposed a distance of about 2 mm to about 6 mm apart.

In a sixth aspect, in addition to one or more of the preceding or following aspects, or in the alternative to some aspects, from 4 to 12 light emitter units are included.

In a seventh aspect, in addition to one or more of the preceding or following aspects, or in the alternative to some aspects, from 4 to 12 peripheral optical detectors are included.

In an eighth aspect, in addition to one or more of the preceding or following aspects, or in the alternative to some aspects, the measured physiological parameter can include at least one of blood oxygen saturation, heart rate, pulse arrival time, systolic blood pressure, respiratory rate, and perfusion index In a ninth aspect, in addition to one or more of the preceding or following aspects, or in the alternative to some aspects, each channel pair defines a particular measurement vector.

In a tenth aspect, in addition to one or more of the preceding or following aspects, or in the alternative to some aspects, the measurement vectors are radially distributed about the central optical detector.

In an eleventh aspect, in addition to one or more of the preceding or following aspects, or in the alternative to some aspects, the measurement vectors are radially spaced 45 degrees apart about the central optical detector.

In a twelfth aspect, in addition to one or more of the preceding or following aspects, or in the alternative to some aspects, the device is configured to be placed onto the chest of a patient.

In a thirteenth aspect, in addition to one or more of the preceding or following aspects, or in the alternative to some aspects, the plurality of light emitter units, the plurality of peripheral optical detectors, and the central optical detector, are mounted together on a flexible substrate.

In a fourteenth aspect, in addition to one or more of the preceding or following aspects, or in the alternative to some aspects, channel pairs of light emitter units and peripheral optical detectors are integrated onto the same circuit board.

In a fifteenth aspect, in addition to one or more of the preceding or following aspects, or in the alternative to some aspects, further comprising an accelerometer, the controller configured to receive input from the accelerometer to mitigate the effects of movement on the measurement of the physiological parameter.

In a sixteenth aspect, in addition to one or more of the preceding or following aspects, or in the alternative to some aspects, the device consumes less power than an otherwise identical system that uses more than one channel pair for measuring a physiological parameter.

In a seventeenth aspect, a method of measuring a physiological parameter of a patient is provided. The method can include placing a reflective optical medical sensor device onto the chest of a patient. The reflective optical medical sensor device can include a central optical detector and a plurality of light emitter units disposed around the central optical detector. Each of the plurality of light emitter units can be disposed a distance from the central optical detector. The reflective optical medical sensor device can also include a plurality of peripheral optical detectors disposed to the outside of the plurality of light emitter units. Each of the plurality of peripheral optical detectors can form a channel pair with one of the plurality of light emitter units. The reflective optical medical sensor device can also include a controller in electrical communication with the central optical detector, the plurality of light emitter units, and the plurality of peripheral optical detectors. The controller can measure the performance of channel pairs; select a particular channel pair; and measure a physiological parameter using the selected channel pair.

In a eighteenth aspect, in addition to one or more of the preceding or following aspects, or in the alternative to some aspects, the controller is further configured to reduce power to the channel pairs not selected to place them into a standby mode.

In a nineteenth aspect, in addition to one or more of the preceding or following aspects, or in the alternative to some aspects, the method can further include placing the reflective optical medical sensor device onto the chest of a patient.

In a twentieth aspect, in addition to one or more of the preceding or following aspects, or in the alternative to some aspects, the controller is further configured to reassess the performance of the selected channel pair at a given time interval to determine if a channel pair in the standby mode reports a better performance than the selected channel pair and the controller can switch from the selected channel pair to a new channel pair if it is determined that the new channel pair reports better performance than the selected channel pair.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

Medical professionals frequently need to monitor a patient's physiological parameters such as blood oxygen saturation, blood pressure, and heart rate during a medical procedure. These types of measurements are often performed using a single sensor. However, measuring physiological parameters, such as those listed above, with a single sensor can result in decreased signal intensity, and increased signal-to-noise ratio (SNR), and thus can potentially provide inaccurate reporting of the parameter values, especially in patients where low perfusion is a problem. Low perfusion—a decrease in blood flow to and from the capillaries—can negatively affect a parameter measurement using a single sensor due to the probability that the sensor only illuminates an area of low blood irrigation within the tissue being monitored.

Additionally, motion can adversely affect measuring physiological parameters. When combined in a patient with low perfusion, the SNR is further confounded and can lead to inaccurate reporting of the physiological parameter being monitored.

In various embodiments herein, multi-sensor devices offer a way to manage perfusion heterogeneity by providing spatial diversity at the measurement site. However, multi-sensor devices can drain battery resources at the expense of more robust measuring capability, depending on how they are operated.

Embodiments herein, however, can include multichannel sensor array devices, configured to optimize the SNR of a single channel within the array while minimizing the drain on battery resources. Embodiments herein can also include an accelerometer to mitigation any of the motion artifacts caused by a patient's movements during a medical procedure.

Figure 1:
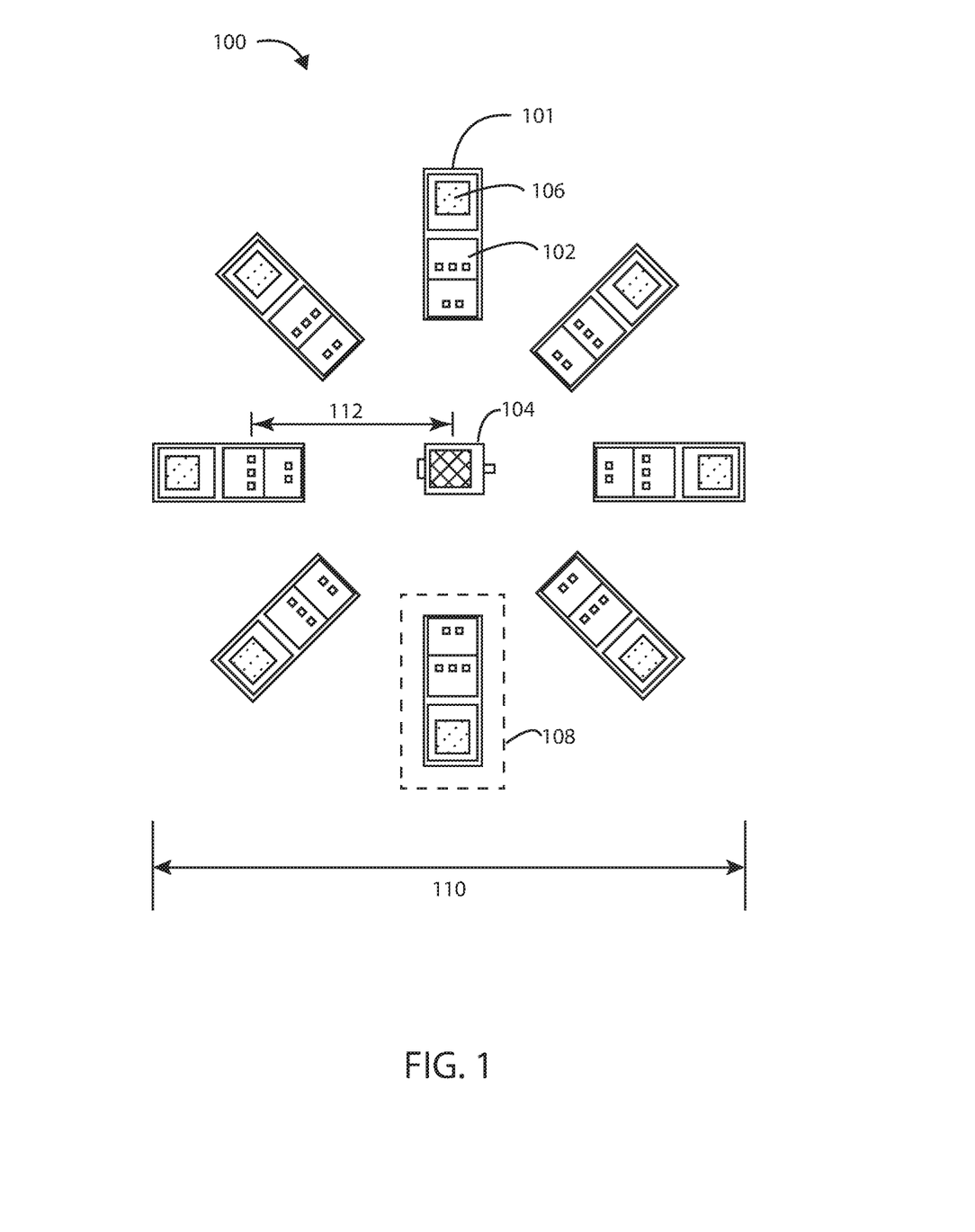
FIG. 1 is a schematic view of an array of multi-wavelength optical sensors in accordance with the embodiments herein.

Referring now to FIG. 1, an array 100 is shown of multi-wavelength optical sensors 101 for use in the reflective optical medical sensors in accordance with the embodiments herein. FIG. 1 illustrates a plurality of multi-wavelength optical sensors 101 that are radially disposed about a central optical detector 104. Each multi-wavelength optical sensor 101 can include a light emitter unit 102 and a peripheral optical detector 106. Each of the peripheral optical detectors 106 can be radially disposed to the outside (e.g., further away from the central optical detector 104) of each of the plurality of light emitter units 102. Each of the peripheral optical detectors 106 can form a channel pair 108 with one of the plurality of light emitter units 102.

In some embodiments, the light emitter units 102 and peripheral optical detectors 106 can be integrated on the same circuit board unit as shown as multi-wavelength optical sensors 101. However, in some embodiments, the light emitter units 102 and peripheral optical detectors 106 can be discrete, stand-alone light emitter or optical detector units, as will be discussed in reference to additional embodiments below.

In some embodiments, the array 100 can include eight light emitter units 102 and eight peripheral optical detectors 106 that are radially disposed about a central optical detector 104, as shown in FIG. 1. In the case of FIG. 1, each channel pair 108 is radially spaced about 45 degrees about the central optical detector 104. In some embodiments, the array 100 can include anywhere from four to twelve light emitter units 102 paired respectively with four to twelve peripheral optical detectors 106 that are radially disposed about a central optical detector 104. Additional embodiments will be discussed below with respect to FIGS. 5-8. It will be appreciated that the arrays 100 can assume many specific physical configurations of light emitter units 102 and peripheral optical detectors 106 radially disposed around a central optical detector 104 and still be within the spirit and scope of the embodiments described herein.

In some embodiments, the array 100 of multi-wavelength optical sensors 101 can have an outer diameter 110 of about 3 cm. In some embodiments, the array 100 of multi-wavelength optical sensors 101 can have an outer diameter of about 1 cm to about 10 cm, or about 2 cm to about 5 cm. The light emitter units 102 can be disposed at a distance 112 from the central optical detector 104. Distance 112 corresponds to the long vector measurements between light emitting units 102 and central optical detector 104. In some embodiments, the light emitter units 102 can be disposed at a distance 112 of about 5 mm to about 13 mm, or 7 mm to about 11 mm from the central optical detector 104. In some embodiments, the light emitter units 102 can be disposed at a distance 112 of about 8 mm to about 10 mm from the central optical detector 104.

Figure 2:
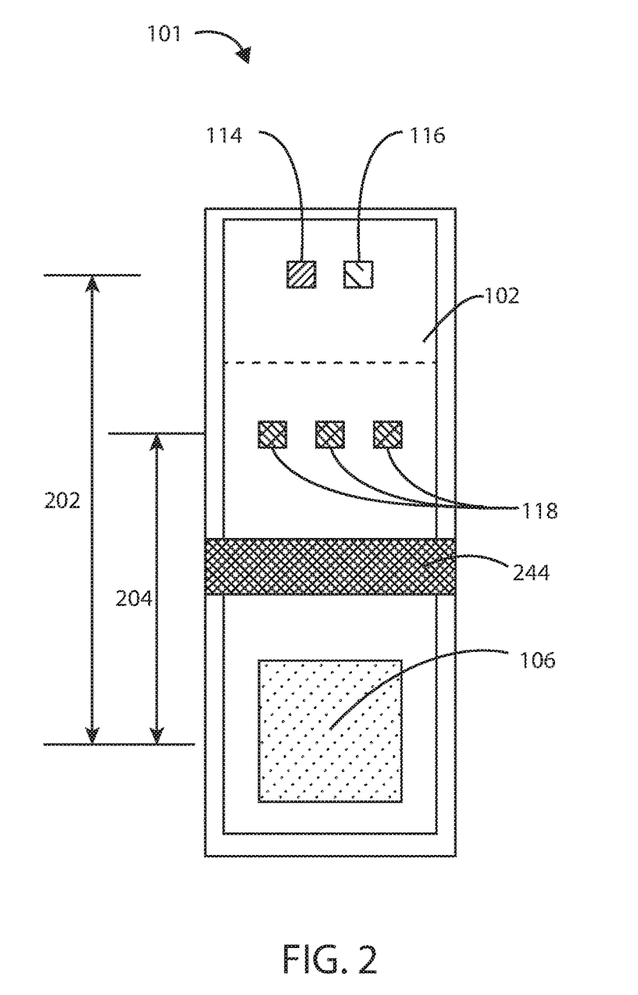
FIG. 2 is a schematic view of a multi-wavelength optical sensor in accordance with the embodiments herein.

Referring now to FIG. 2, an illustration of an individual multi-wavelength optical sensor 101 is shown in accordance with the embodiments herein. Multi-wavelength optical sensor 101 can include a light emitter unit 102 and a peripheral optical detector 106, forming a channel pair. The light emitter unit 102 can include one or more light emitters that emit light having one or more wavelengths. As shown in FIG. 2, a first light emitter 114 and a second light emitter 116 can be disposed at a distance 202 from peripheral optical detector 106. Similarly, light emitters 118 can be disposed at a distance 204 from peripheral optical detector 106. In some embodiments, the light emitter unit 102 and peripheral optical detector 106 of each channel pair can be disposed at a distance of about 2 mm to about 6 mm apart. In some embodiments, light emitter unit 102 and peripheral optical detector 106 of each channel pair can be disposed at a distance of about 3 mm to about 5 mm apart.

Light emitter unit 102 can include multiple light emitters, including a first light emitter 114 configured to emit light at a first wavelength of peak emission, a second light emitter 116 configured to emit light at a second wavelength of peak emission, and a third light emitter 118 configured to emit light at a third wavelength of peak emission. In some embodiments, first light emitter 114, second light emitter 116, and third light emitter 118 may include one or more light emitters that can emit light at the same wavelength to deliver higher light output at that wavelength. In some embodiments, light emitter unit 102 can include a first light emitter 114 that delivers infrared (IR) light, a second light emitter 116 that delivers red light, and one or more third light emitters 118 that deliver green light, as shown in FIG. 2.

The first light emitter 114 can be configured to emit IR light. The IR light can be at various specific wavelengths, but as a specific example, at a wavelength of peak emission ($\lambda_{peak}$) of 800 to 1000 nm, 900 to 1000 nm, 940 to 960 nm, or 950 nm as a more specific example, at a temperature of (T=25° C.) and a forward current ($I_F$) of 20 mA. It will be appreciated that various specific currents can be used. In various embodiments, the forward current provided to the first light emitter can be equal to or less than 150 mA, 100 mA, 90 mA, 80 mA, 70 mA, 60 mA, 50 mA, 40 mA, 30 mA, 20 mA, 10 mA or 5 mA. In some embodiments, the forward current provided to the first light emitter can be in a range between any of the foregoing values.

In various embodiments the first light emitter 114 can be configured to have spectral bandwidth at half peak ($\Delta\lambda$) of 30 to 54 nm, 34 to 50 nm, or 38 to 46 nm, or 42 nm as a specific example ($I_F$=20 mA, T=25° C., and a time to peak emission ($t_p$) of 20 ms). In various embodiments, the first light emitter can exhibit substantial wavelength stability (delta lambda) with temperature.

The second light emitter 116 can be configured to emit light at various wavelengths. In some embodiments, the second light emitter can be configured to emit red light having a $\lambda_{peak}$ of 622 to 700, or 650 to 670 nm, or 660 nm as a specific example ($I_F$=20 mA, T=25° C.). The second light emitter 116 can be configured to have a $\Delta\lambda$ of 10 to 24 nm, 15 to 19 nm, or 17 nm as a specific example ($I_F$=20 mA, T=25° C.). In various embodiments, the second light emitter can exhibit substantial wavelength stability (delta lambda) with temperature.

In various embodiments, the forward current provided to the second light emitter can be equal to or less than 150 mA, 100 mA, 90 mA, 80 mA, 70 mA, 60 mA, 50 mA, 40 mA, 30 mA, 20 mA, 10 mA or 5 mA. In some embodiments, the forward current provided to the second light emitter can be in a range between any of the foregoing values.

The third light emitter(s) 118 can be configured to emit light at various wavelengths. In some embodiments, the third light emitter(s) 118 can be configured to emit green light having a $\lambda_{peak}$ of 492 to 577 nm, or 520 to 540 nm, or 530 nm as a specific example ($I_F$=20 mA, T=25° C.). The third light emitter(s) can be configured to have a $\Delta\lambda$ of 28 to 40, or 32 to 36, or 34 nm as a specific example ($I_F$=20 mA, T=25° C.).

In various embodiments, the forward current provided to the third light emitter can be equal to or less than 150 mA, 100 mA, 90 mA, 80 mA, 70 mA, 60 mA, 50 mA, 40 mA, 30 mA, 20 mA, 10 mA or 5 mA. In some embodiments, the forward current provided to the third light emitter can be in a range between any of the foregoing values.

It will be appreciated that the third light emitter can also, in some embodiments, emit light at wavelengths associated with colors other than green. For example, in some embodiments, the third light emitter can emit light at wavelengths associated with the color blue (e.g., 455 to 492 nm).

Peripheral optical detector 106 can be configured to have a spectral range of sensitivity of various specific values including 200 to 1300 nm, or 400 to 1100 nm (T=25° C.).

As discussed above, the light emitter units 102 and peripheral optical detectors 106 can be formed of a single, integrated unit as shown in multi-wavelength optical sensor 101 or as discrete, stand-alone light emitter or optical detector units. In the case of an integrated unit, the light emitter unit 102 and optical detector 106 can be optically separated by an opaque optical barrier 244 to prevent absorption of the emitted light from light emitter units 102. One example of an integrated multi-wavelength optical sensor for use in the embodiments herein can include SFH7060, by OSRAM Opto Semiconductors of Sunnyvale, Calif. However, many different specific optical sensors are contemplated herein.

Figure 3:
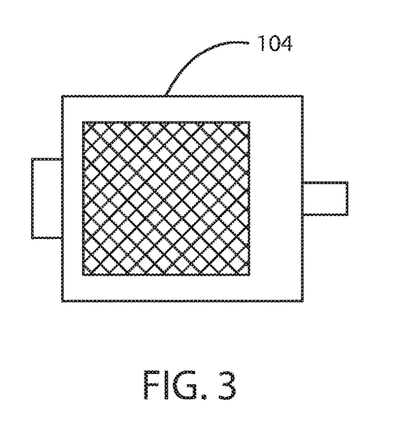
FIG. 3 is a schematic view of a central optical detector in accordance with the embodiments herein.

Referring now to FIG. 3, an illustration of a central optical detector 104 is shown. Like peripheral optical detector 106, central optical detector 104 can be configured to have a spectral range of sensitivity of various specific values including 200 to 1300 nm or 400 to 1100 nm (T=25° C.). An exemplary central optical detector for use in the embodiments herein can include the silicon pin photodiode BPW 34 SR, by OSRAM Opto Semiconductors of Sunnyvale, Calif. However, it will be appreciated that many different specific optical detectors are contemplated herein.

Figure 4:
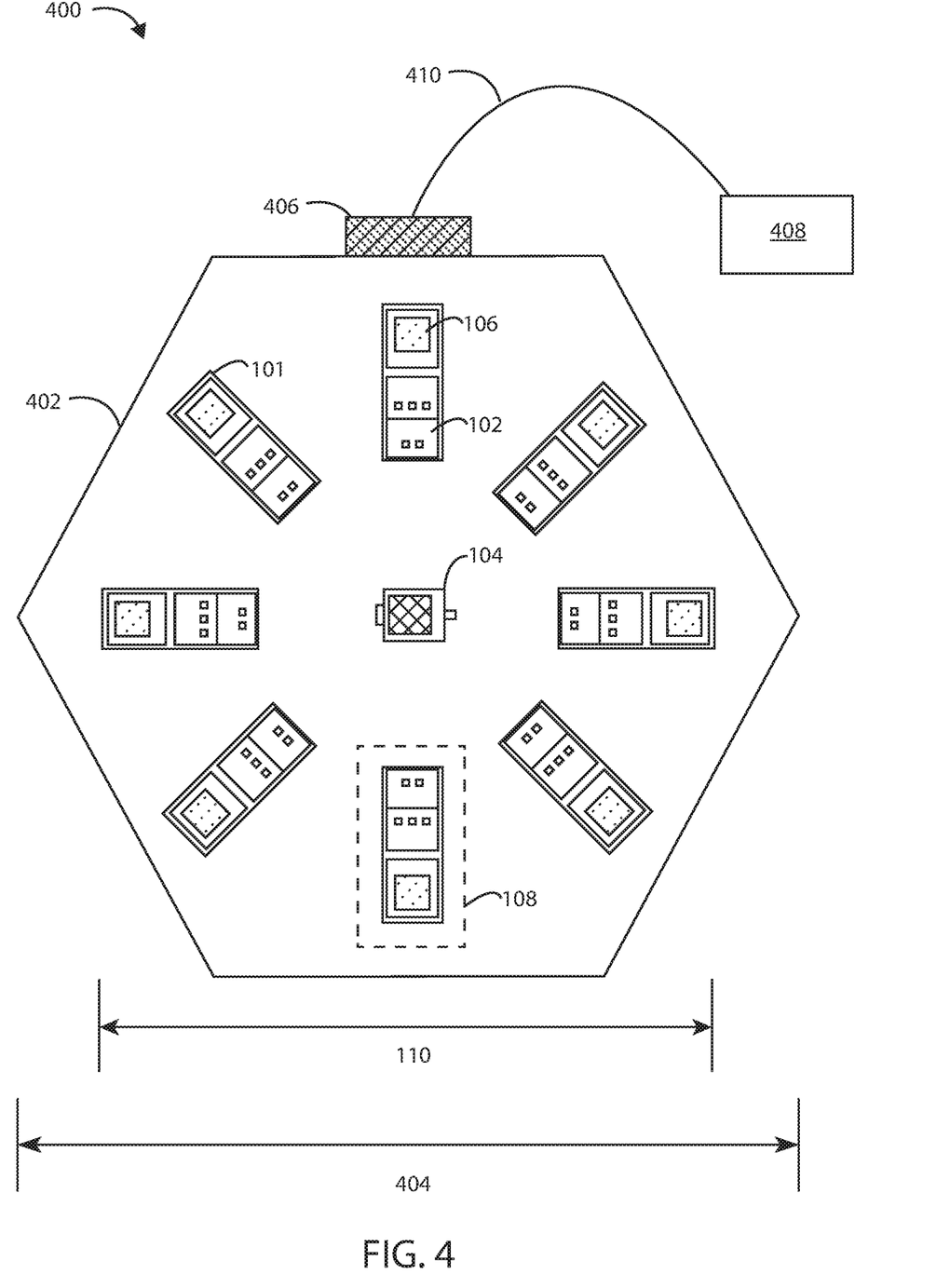
FIG. 4 is a schematic view of a reflective optical medical sensor in accordance with the embodiments herein.

Referring now to FIG. 4, an illustration of a reflective optical medical sensor 400 in accordance with the embodiments herein is shown. An array of multi-wavelength optical sensors 101, each having a light emitter unit 102 and peripheral optical detector 106, is shown radially disposed about a central optical detector 104. The plurality of light emitter units 102, the plurality of peripheral optical detectors 106, and the central optical detector 104 are shown mounted on a substrate 402. Substrate 402 can be formed from a flexible or stretchable material. In some embodiments, substrate 402 can be formed from, but not be limited to, flexible polymers such as polyethylene terephthalate, polycarbonate, polyurethane, polydimethylsiloxane, silicone rubbers, and the like. In some embodiments, substrate 402 can be formed of a flexible or stretchable material and can further include a stiffener on the side opposing the light emitter units and optical detectors to provide an added layer of structural support for the components. Alternatively, in some embodiments, substrate 402 can be formed of a rigid material.

In some embodiments, the diameter 404 of the reflective optical medical sensor 400 can be about 3 cm. In some embodiments, the diameter 404 of the reflective optical medical sensor 400 can be about 1 cm to about 5 cm. In some embodiments, the diameter 110 of the array of multi-wavelength optical sensors 101 can be the same as the diameter 404 of the reflective optical medical sensor 400. In some embodiments, the diameter 110 of the array of multi-wavelength optical sensors 101 can be different than the diameter 404 of the reflective optical medical sensor 400.

Reflective optical medical sensor 400 can include an extended tail piece connector 406 to allow for connection 410 to an analog front end controller module 408. An exemplary analog front end controller module for use in the embodiments herein can include the AFE4405 controller by Texas Instruments, Inc., of Dallas, Tex. It will be appreciated that the controller 408 can be in electrical communication with the central optical detector, the plurality of light emitter units, and the plurality of peripheral optical detectors. The controller 408 can be configured to measure performance of the channel pairs, select a channel pair, and measure a physiological parameter using the selected channel pair. Connection 410 can provide a hardwired or wireless communication connection between the reflective optical medical sensor 400 and controller 408.

Figure 5:
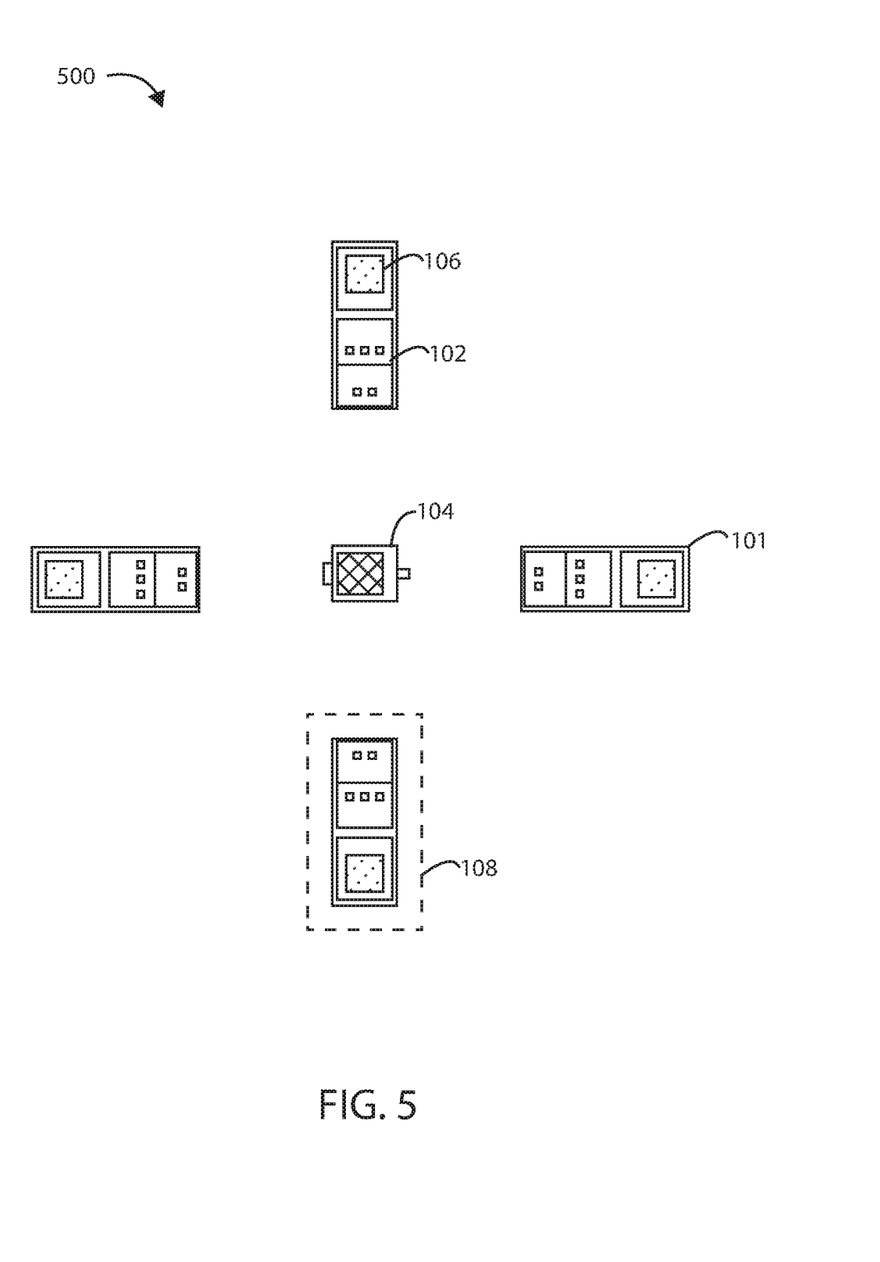
FIG. 5 is a schematic view of another array of multi-wavelength optical sensors in accordance with the embodiments herein.
Figure 6:
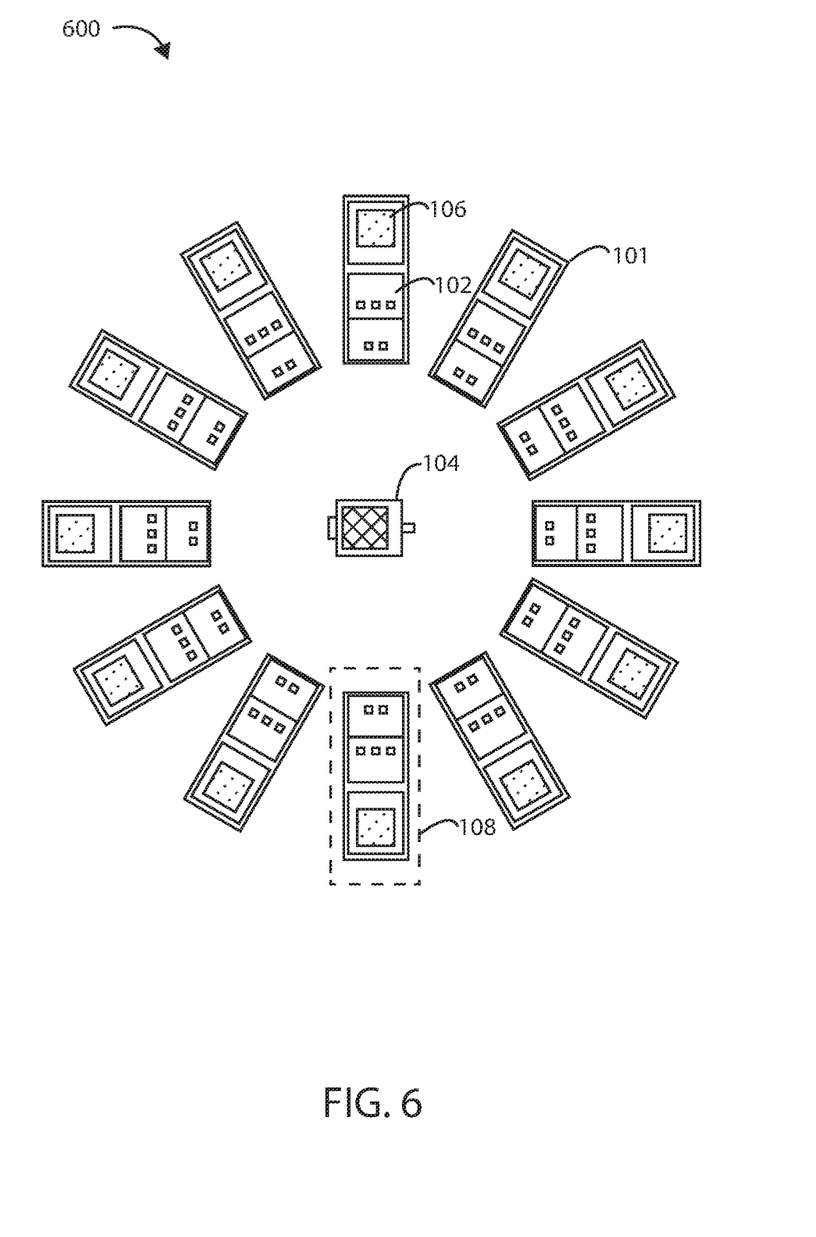
FIG. 6 is a schematic view of another array of multi-wavelength optical sensors in accordance with the embodiments herein.
Figure 7:
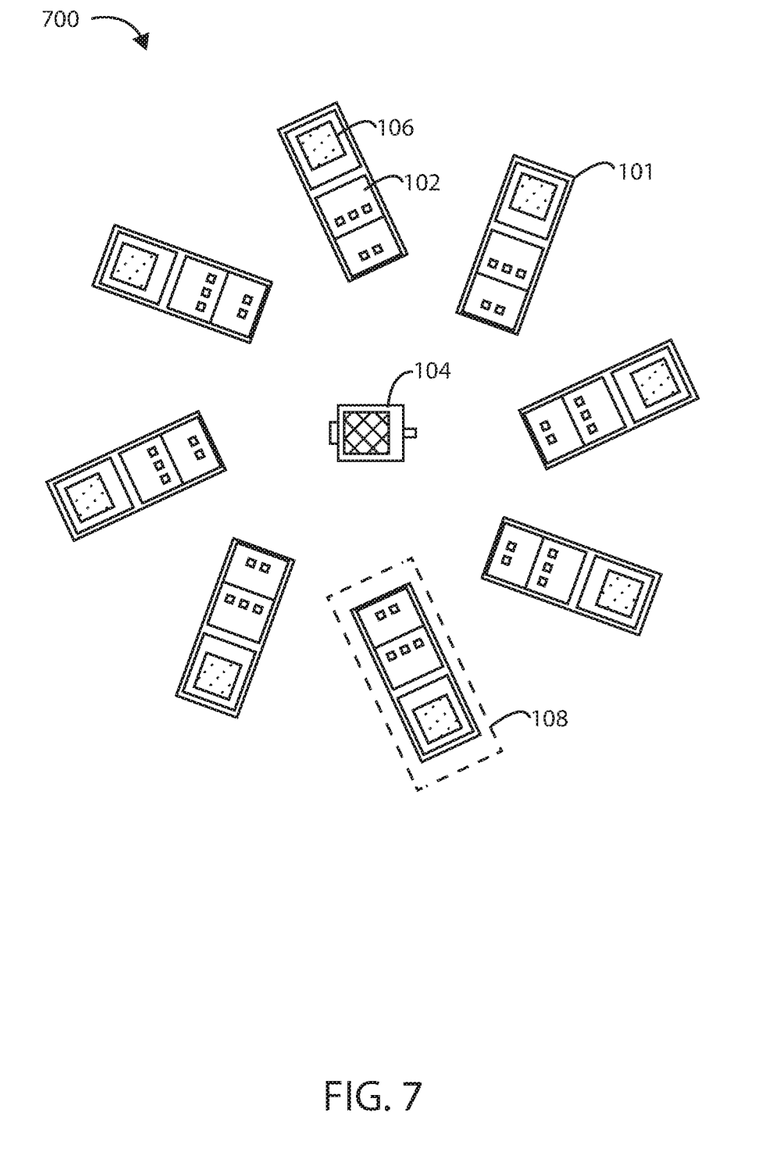
FIG. 7 is a schematic view of another array of multi-wavelength optical sensors in accordance with the embodiments herein.

Referring now to FIGS. 5-8, additional embodiments of the array of multi-wavelength optical sensors 101 are shown. FIG. 5 shows array 500 having four multi-wavelength optical sensors 101 radially spaced about 90 degrees about the central optical detector 104. FIG. 6 shows array 600 having twelve multi-wavelength optical sensors 101 radially spaced about 30 degrees about the central optical detector 104. FIG. 7 shows array 700 having eight multi-wavelength optical sensors 101 radially spaced about 45 degrees about the central optical detector 104, and additionally shows each pair rotated about its short axis by about 25 degrees.

Figure 8:
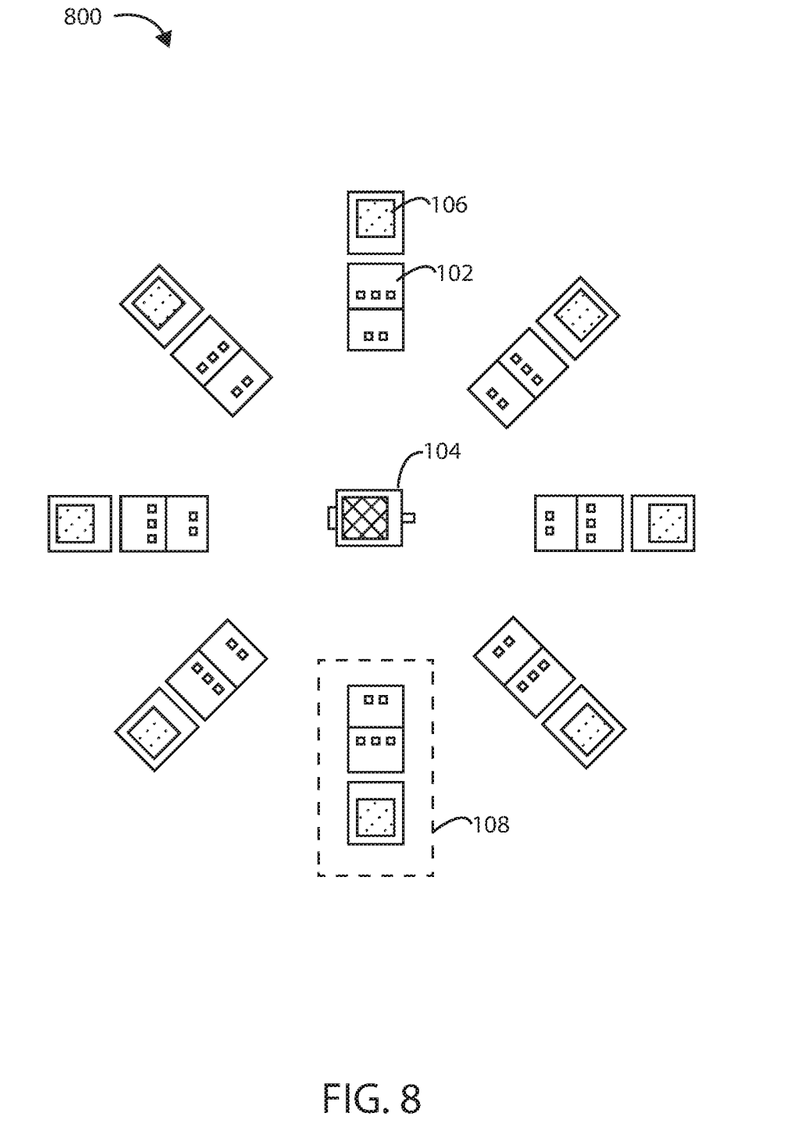
FIG. 8 is a schematic view of another array of multi-wavelength optical sensors in accordance with the embodiments herein.

FIG. 8 shows array 800 having eight sets of light emitter units 102 and peripheral optical detectors 106 radially spaced about 45 degrees about the central optical detector 104. In FIG. 8, each light emitter unit 102 a peripheral optical detector 106 of each channel pair 108 is a discrete, stand-alone unit.

Figure 9:
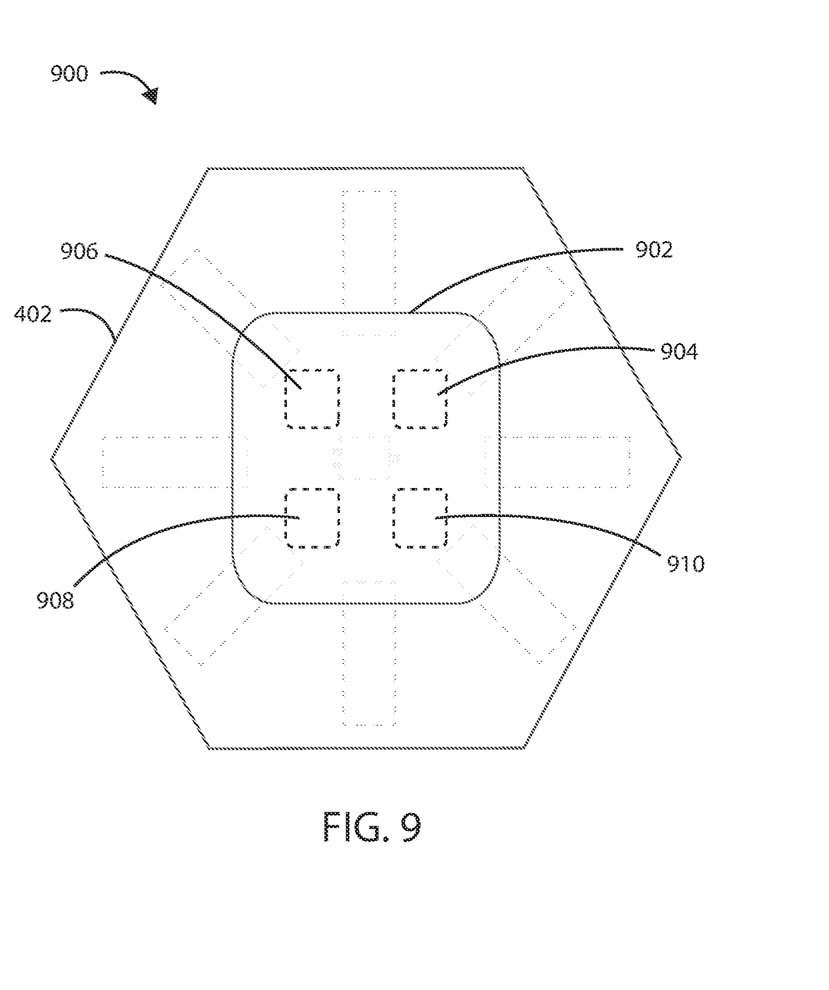
FIG. 9 is a schematic view of a reflective optical medical sensor in accordance with the embodiments herein.

Referring now to FIG. 9, an illustration of a reflective optical medical sensor 900 in accordance with the embodiments herein is shown. Reflective optical medical sensor 900 is shown having a housing 902 affixed to the backside of the array of multi-wavelength optical sensors 101. An accelerometer 904 can be disposed within the housing and can detect motion of the reflective optical medical sensor 900 and provide those measurements to a controller for use in mitigating signal noise due to effects of movement on the measurement of the physiological parameter. Some examples of motion artifacts can include, but not be limited to foot strike during running or walking, standing up from a seated position, lying down from a standing or seated position, and the like.

It will be appreciated that various other components can also be disposed within the housing 902. By way of example, in some embodiments, a controller 906 (in addition to or instead of an external controller such as that shown in FIG. 4), a power source 908 (which can include, but is not limited to, a battery, a capacitor, a power interface circuit, or the like), and/or a telemetry circuit 910, amongst others.

Photoplethysmogram Oximetry

Reflective optical medical sensors described herein can be used for example when performing reflective photoplethysmogram (PPG) oximetry. PPG oximetry is a minimally invasive technique that can be used to measure blood oxygen saturation (reported as oxygen saturation, or $SpO_2$), heart rate (in beats per minute, i.e., bpm), pulse arrival time, R-R interval, systolic blood pressure, respiratory rate, perfusion index (the ration of pulsatile blood flow to non-pulsatile blood flow), and the like. PPG can additionally be used to measure the volume of a vessel or an organ. In some embodiments, PPG oximetry can be performed on the chest. In some embodiments, the PPG oximetry can be performed on the chest, specifically over the sternum. PPG oximetry can also be performed on a number of additional sites on the body, including, but not limited to the wrist, the fingertip, the forehead, the arm, the ear and the like.

Generally PPG oximetry is a technique that involves shining one or more wavelengths of light into the skin of a patient and measures the changes in light absorption due to the changes in blood volume at the measurement site. Different wavelengths of light penetrate the tissues at different depths at the measurement site, and thus provide opportunities to measure different physiological parameters. Blood volume at the measurement site can be monitored throughout the cardiac cycle. As the heart contracts during systole, blood is ejected from the left ventricle and is circulated through the arteries. As the heart relaxes during diastole, blood is pulled from the peripheral arteries, through the veins, and drawn back to the heart. Thus, as blood is ejected out of the heart, more blood will flow through the arteries than when the heart relaxes and draws blood back to the heart.

The changes in light absorption due to the changes in blood volume in the arteries and/or arterioles at the measurement site can be determined by illuminating the arteries beneath the surface of the skin with one or more wavelengths of light at various times throughout the cardiac cycle. Different diodes having different wavelengths of peak emission can be chosen depending on the physiological parameter to be tested. Analysis can be performed using the data collected from the light absorbed, the light reflected, and the light scattered during illumination to determine one or more of the physiological parameters listed above.

In one example, blood oxygen saturation ($SpO_2$) can be determined by dual-wavelength illumination of the arteries and/or arterioles in the subcutaneous tissue. During each cardiac cycle, as blood is pumped by the heart into the periphery the pulse pressure provides enough force to enlarge the arteries and/or arterioles Hemoglobin in the blood can absorb light of various wavelengths. To measure $SpO_2$, a PPG device can be used to shine light having wavelengths at or about 660 nm and 950 nm on a specific location, such as the chest or wrist. Absorption of light at that location can be influenced by the level of oxygen saturation of the hemoglobin in the blood in close proximity to the detector(s). Hemoglobin is an oxygen-carrying metalloprotein found in healthy, circulating red blood cells. Each molecule of hemoglobin can carry up to four molecules of oxygen. In a deoxygenated state, hemoglobin absorbs light at or about a wavelength of 660 nm. In an oxygenated state, hemoglobin absorbs light at or about a wavelength of 950 nm. The difference in the amount of absorbance for each wavelength, can be used to calculate a percentage of $SpO_2$ at any given time. The amount of light absorbed can be determined experimentally by analyzing total reflected light at the optical detector. The reflective optical medical sensors described herein can be configured to use the data collected to calculate the percentage $SpO_2$.

In another example, heart rate can be determined by illumination of the arteries and/or arterioles with green light. During each cardiac cycle, as the blood flowing into and out of the underlying arteries and/or arterioles is illuminated with light having a wavelength at or about 530 nm, absorption of the light by the hemoglobin in the blood changes depending on the volume of blood at the measurement site. As blood flows into the measurement site during a heartbeat, the light absorption is greater than it is when the heart is relaxed and blood flow at the measurement site. The reflective optical medical sensors described herein can be configured to illuminate the site in excess of hundreds of times per second and use the data collected to correlate absorption at a given time period with heart rate.

Measurement Vectors

The light emitter units and optical detectors (peripheral and central) described herein can create discrete measurement vectors for each location in the array around the central optical detector. In some embodiments, each channel pair defines one or more measurement vectors. In some embodiments, the measurement vectors are radially distributed about the central optical detector. In some embodiments, the measurement vectors are radially spaced 45 degrees apart about the central optical detector in about the same location as the channel pairs. In some embodiments, the vectors are radially spaced about 33, 36, 40, 45, 51, 60, 72, or 90 degrees apart about the central optical detector in the same location as the channel pairs.

Figure 10:
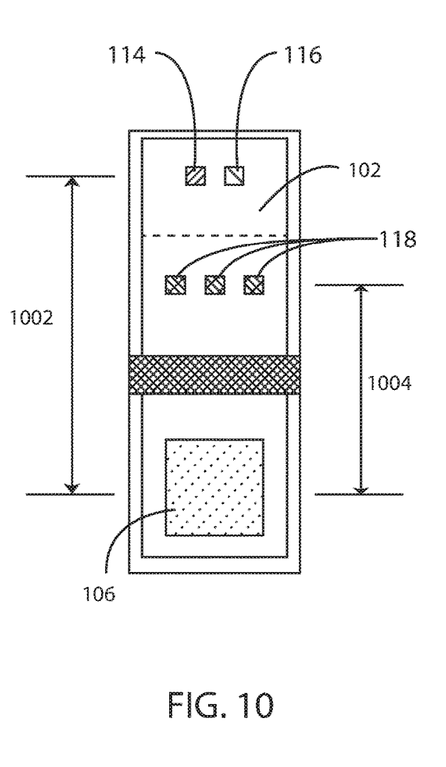
FIG. 10 is a schematic view of the short vector associations in accordance with the embodiments herein.

Referring now to FIG. 10, a schematic representation is shown of the types of short vectors that can be generated in accordance with the embodiments herein. For example, FIG. 10 shows light emitters 114 and 116 spaced at a distal short vector distance 1002 from the peripheral optical detector 106. FIG. 10 additionally shows light emitters 118 spaced at a proximal short vector distance 1004 from peripheral optical detector 106. In some embodiments, the distal short vector distance 1002 from light emitters 114 and 116 to peripheral optical detector 106 can be about 2 mm to about 7 mm, or about 4 mm to about 7 mm. In some embodiments, the distal short vector distance 1002 can be any of 4, 5, 6, or 7 mm from peripheral optical detector 106 or in a range between any of the foregoing. In some embodiments, the proximal short vector distance 1004 from light emitters 118 to peripheral optical detector 106 can be about 0.5 mm to about 3 mm. In some embodiments, the proximal short vector distance 1004 can be any of 0.5, 1, 2, or 3 mm from peripheral optical detector 106 or in a range between any of the foregoing.

Figure 11:
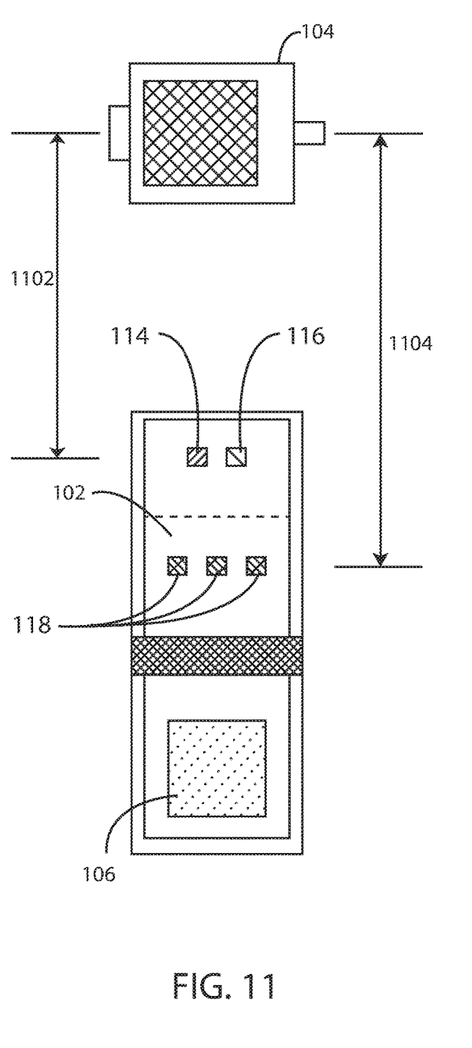
FIG. 11 is a schematic view of the long vector associations in accordance with the embodiments herein.

Similarly, FIG. 11 shows a schematic representation of the types of long vectors that can be generated in accordance with the embodiments herein. For example, FIG. 11 shows light emitters 114 and 116 spaced at a proximal long vector distance 1102 from the central optical detector 104. FIG. 11 additionally shows light emitters 118 spaced at a distal long vector distance 1104 from central optical detector 104. In some embodiments, the proximal long vector distance 1102 from light emitters 114 and 116 to central optical detector 104 can be about 8 mm to about 9 mm. In some embodiments, the proximal long vector distance 1102 can be any of 8 or 9 mm from central optical detector 104. In some embodiments, the distal long vector distance 1104 from light emitters 118 to central optical detector 104 can be about 10 mm to about 14 mm. In some embodiments, the distal long vector distance 1104 can be any of 10, 11, 12, 13, or 14 mm from central optical detector 104 or within a range between any of the foregoing.

Vector Scoring and Power Optimization

The array of channel pairs contained within the reflective optical medical sensors described herein can provide spatial diversity for both long and short vector measurements, as discussed above. Having multiple measurement options can be important when trying to manage perfusion heterogeneity within an individual and within a population. Perfusion is the process by which the heart delivers blood to the capillary beds during the cardiac cycle. Low perfusion—when there is a decrease in blood flow to and from the capillaries—is a common phenomenon in individuals with heart conditions, diabetes, obesity, arterial disorders, circulation problems, and the like. Low perfusion is also common in elderly populations and during exposure to cold environments.

Low perfusion can cause a low signal-to-noise ratio (SNR) and thus interfere with accurate detection of physiological parameters. To optimize signal detection, an array of channel pairs taking multiple measurements over a larger surface area can help mitigate the low perfusion, and thus low SNR; however, the demand on the battery life can be very high if all channels are utilized at the same time. One way to preserve battery power and to keep costs and resources to a minimum, is to configure the reflective optical medical sensors described herein to undergo an indexing step to choose an optimal channel pair for use during measurements of a physiological parameter. It will be appreciated that additional optimization steps can also be configured into the reflective optical medical sensors, preceding or following the indexing step.

Briefly, the indexing step can include utilizing a software controlled switch, such as an inter-integrated circuit ($I^2C$) or other similar device, to apply power to each channel pair in the array and measure the short and long vector data obtained for each channel pair. Each channel pair can be interrogated multiple times to obtain an average score at each location in the array.

A determination can be made as to which channel pair shows the best score having the highest SNR and lowest current draw. Once determined as the best channel pair, the remaining channel pairs can be relegated to a standby mode, wherein they draw little to no current from the battery and thus help to optimize power consumption. Choosing a single best channel pair as described can ensure that the reflective optical medical sensor device described herein consumes less power than an otherwise identical system that uses more than one channel pair for measuring a physiological parameter.

In some embodiments, the scoring of the channel pairs can be stored by the device for later use or reporting. For example, after a particular channel pair is selected as having the best score, if later a new channel pair needs to be selected, then what was previously the next best channel pair can be assessed first in an effort to most quickly find the best channel pair for use.

A calibration step can be performed on the chosen channel pair, and it can then be utilized during the duration of measuring the chosen physiological parameter(s). If at any time during the measurement it should be determined that the initially chosen channel pair is no longer optimal, the indexing step can be repeated to reassess if a different channel pair reports a new best score. If a different channel pair reports a new best score, the new channel pair can be chosen as the preferred channel pair for subsequent measurements, and the remainder of channel pairs can be relegated to standby mode. In some embodiments, it will be appreciated that a vector pattern for the entire array can be provided as a reference to show the level of perfusion for any given channel pair at any given point in time.

Reflective Optical Medical Sensor

The reflective optical medical sensor devices described herein are suited for taking PPG measurements at the sternal region of the chest of a patient. In some embodiments, the reflective optical medical sensor devices can take PPG measurements elsewhere on or in a patient's body. The reflective optical medical sensor device can be a patch sensor temporarily affixed to the patient by an adhesive, or it can be a garment worn with or integrated into other monitoring systems. Other monitoring systems can include those used for echocardiography (ECG), ballistocardiography (BCG), seismocardiography (SCG), electrogastrography (EGG), and similar sensor-based detection systems.

Figure 12:
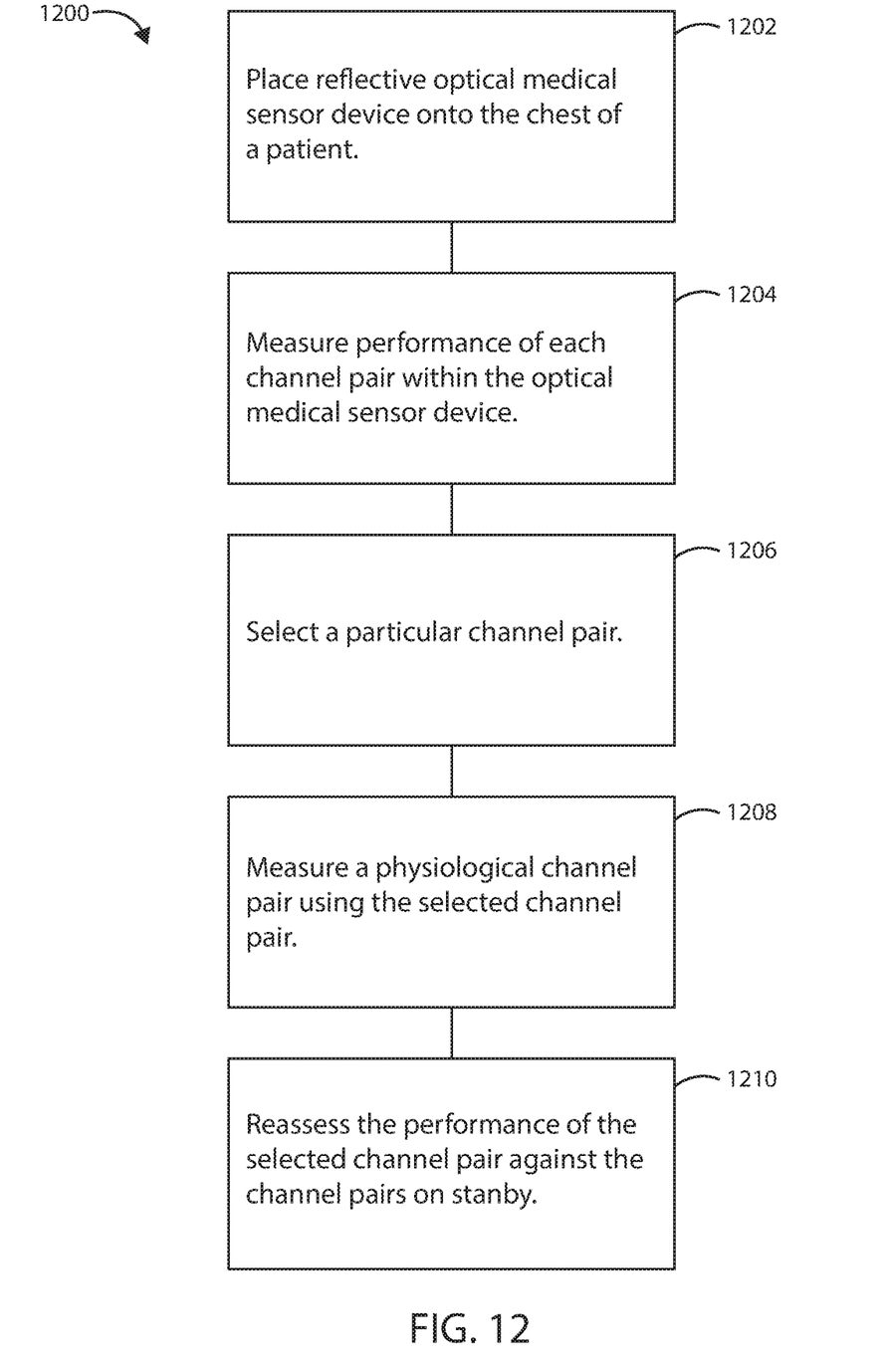
FIG. 12 is a flow diagram of a method of using a reflective optical medical device in accordance with the embodiments herein.

The reflective optical medical sensor devices described herein can be used in a method of measuring a physiological parameter of a patient. FIG. 12 shows a flow diagram of a method 1200 for using the reflective optical medical sensor devices in accordance with the embodiments herein. The method can include placing a reflective optical medical sensor device onto the chest of a patient at 1202. The reflective optical medical sensor device can include the features described elsewhere herein, including a central optical detector and a plurality of light emitter units disposed around the central optical detector. Each of the plurality of light emitter units can be disposed a distance from the central optical detector. A plurality of peripheral optical detectors can be disposed to the outside of each of the plurality of light emitter units. Each of the plurality of peripheral optical detectors can form a channel pair with one of the plurality of light emitter units. The reflective optical medical sensor can also include a controller in electrical communication with the central optical detector, the plurality of light emitter units, and the plurality of peripheral optical detectors.

The controller can be configured to perform a number of steps throughout the method described herein. In some embodiments, the controller can measure the performance of channel pairs at 1204. Measuring the performance of the channel pairs can include applying power to each channel pair in the array and measuring the short and long vector data obtained for each channel pair. Each channel pair can be interrogated multiple times to obtain an average score at each location in the array. Upon determining the which channel pair shows the best score having the highest SNR and lowest current draw, the controller can select a particular channel pair at 1206. In some embodiments, the controller can be configured to reduce power to all channel pairs other than the selected channel pair. In some embodiments, the controller can be configured to calibrate the selected channel pair prior to measuring a particular physiological parameter using the selected channel pair at 1208.

In some embodiments, the controller can be configured to reassess the performance of the selected channel pair at a given time interval to determine if a channel pair in the standby mode reports a better performance than the selected channel pair at 1210. Performance can be assessed according to SNR, and in some cases SNR as indexed by current where lower current is better. If the controller determines that a different channel pair reports better performance than the selected channel pair at, the controller can switch from the selected channel pair to a new channel pair and return to step 1208 and proceed with measuring a physiological channel. If the controller determines that the selected channel pair continues to exhibit the best performance of all channel pairs, then the controller can continue to measure the physiological parameter until it is determined that enough measurements have been made or until there is no longer a need to monitor that particular physiological parameter. In some embodiments, the controller can also be configured to record the physiological data measured by the selected pair.

The embodiments described herein are not intended to be exhaustive or to limit the invention to the precise forms disclosed in the following detailed description. Rather, the embodiments are chosen and described so that others skilled in the art can appreciate and understand the principles and practices. Aspects have been described with reference to various specific and preferred embodiments and techniques. However, it should be understood that many variations and modifications may be made while remaining within the spirit and scope herein.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference. Nothing herein is to be construed as an admission that the inventors are not entitled to antedate any publication and/or patent, including any publication and/or patent cited herein.

The invention claimed is:

1. A reflective optical medical sensor device comprising:
   a central optical detector;
   a plurality of light emitter units disposed radially around the central optical detector, each of the plurality of light emitter units disposed a distance from the central optical detector,
   a plurality of peripheral optical detectors disposed to an outside of the plurality of light emitter units with respect to the central optical detector such that the peripheral optical detectors are disposed further away from the central optical detector than the light emitter units, each of the plurality of peripheral optical detectors forming a channel pair with one of the plurality of light emitter units;
   wherein the plurality of light emitter units comprise a plurality of distal light emitter units disposed radially around the central optical detector at a distal long vector distance and a plurality of proximal light emitter units disposed radially around the central optical detector at a proximal long vector distance;
   wherein the distal long vector distance is greater than the proximal long vector distance;
   wherein the peripheral optical detectors are disposed further away from the central optical detector than the plurality of distal light emitter units and the plurality of proximal light emitter units; and
   wherein each of the plurality of peripheral optical detectors forms a channel pair with one of the plurality of distal light emitter units and one of the plurality of proximal light emitter units; and
   a controller in electrical communication with the central optical detector, the plurality of light emitter units, and the plurality of peripheral optical detectors;
   wherein each channel pair of light emitter units and peripheral optical detectors is integrated together on a same circuit board;
   wherein the controller is configured to
     measure performance of channel pairs across short vectors and long vectors, the short vector comprising the peripheral optical detector and the light emitter unit of the channel pair and the long vector comprising the light emitter unit of the channel pair and the central optical detector, wherein each of the long vectors span a greater distance than each of the short vectors;
     select a particular channel pair; and
     measure a physiological parameter using the selected channel pair.

2. The reflective optical medical sensor device of claim 1, each of the plurality of light emitter units comprising a first light emitter configured to emit light at a first wavelength max of peak emission, a second light emitter configured to emit light at a second wavelength of peak emission, and a third light emitter configured to emit light at a third wavelength of peak emission.

3. The reflective optical medical sensor device of claim 2, wherein the first wavelength of peak emission is from 940 to 960 nm, the second wavelength of peak emission is from 650 to 670 nm, and the third wavelength of peak emission is from 520 to 540 nm.

4. The reflective optical medical sensor device of claim 1, each of the plurality of light emitter units disposed a distance from the central optical detector of about 7 mm to about 11 mm.

5. The reflective optical medical sensor device of claim 1, wherein the light emitter unit and peripheral optical detector of each channel pair is disposed a distance of 2 mm to 6 mm apart.

6. The reflective optical medical sensor device of claim 1, comprising from 4 to 12 light emitter units.

7. The reflective optical medical sensor device of claim 1, comprising from 4 to 12 peripheral optical detectors.

8. The reflective optical medical sensor device of claim 1, the measured physiological parameter including at least one of blood oxygen saturation, heart rate, pulse arrival time, systolic blood pressure, respiratory rate, and perfusion index.

9. The reflective optical medical sensor device of claim 1, wherein each channel pair defines a particular measurement vector.

10. The reflective optical medical sensor device of claim 9 wherein the measurement vectors are radially distributed about the central optical detector.

11. The reflective optical medical sensor device of claim 1, wherein the short vectors and long vectors are radially spaced 45 degrees apart about the central optical detector.

12. The reflective optical medical sensor device of claim 1, wherein the device is configured to be placed onto the chest of a patient.

13. The reflective optical medical sensor device of claim 1, wherein the plurality of light emitter units, the plurality of peripheral optical detectors, and the central optical detector, are mounted together on a flexible substrate.

14. The reflective optical medical sensor device of claim 1, further comprising an accelerometer, the controller configured to receive input from the accelerometer to mitigate the effects of movement on the measurement of the physiological parameter.

15. The reflective optical medical sensor device of claim 1, wherein the device consumes less power than an otherwise identical system that uses more than one channel pair for measuring a physiological parameter.

16. The reflective optical medical sensor device of claim 1, the plurality of distal light emitter units spaced at a distal short vector distance from the paired peripheral optical detector, and the plurality of proximal light emitter units spaced at a proximal short vector distance from the paired peripheral optical detector.

17. A method of measuring a physiological parameter of a patient, the method comprising
   placing a reflective optical medical sensor device on or in a patient, the reflective optical medical sensor device comprising:
     a central optical detector;
     a plurality of light emitter units disposed radially around the central optical detector, each of the plurality of light emitter units disposed a distance from the central optical detector,
     a plurality of peripheral optical detectors disposed to an outside of the plurality of light emitter units with respect to the central optical detector such that the peripheral optical detectors are disposed further away from the central optical detector than the light emitter units, each of the plurality of peripheral optical detectors forming a channel pair with one of the plurality of light emitter units;

wherein the plurality of light emitter units comprise a plurality of distal light emitter units disposed radially around the central optical detector at a distal long vector distance and a plurality of proximal light emitter units disposed radially around the central optical detector at a proximal long vector distance;

wherein the distal long vector distance is greater than the proximal long vector distance;

wherein the peripheral optical detectors are disposed further away from the central optical detector than the plurality of distal light emitter units and the plurality of proximal light emitter units; and wherein each of the plurality of peripheral optical detectors forms a channel pair with one of the plurality of distal light emitter units and one of the plurality of proximal light emitter units; and a controller in electrical communication with the central optical detector, the plurality of light emitter units, and the plurality of peripheral optical detectors;

measuring performance of channel pairs across short vectors and long vectors, the short vector comprising the peripheral optical detector and the light emitter unit of the channel pair and the long vector comprising the light emitter of the channel pair and the central optical detector, wherein each of the long vectors span a greater distance than each of the short vectors;

selecting a particular channel pair; and measuring a physiological parameter using the selected channel pair.

18. The method of claim 17, wherein the controller is further configured to reduce power to the channel pairs not selected to place them into a standby mode.

19. The method of claim 17, comprising placing the reflective optical medical sensor device onto the chest of a patient.

20. The method of claim 17, wherein the controller is further configured to reassess the performance of the selected channel pair at a given time interval to determine if a channel pair in the standby mode reports a better performance than the selected channel pair; and wherein the controller can switch from the selected channel pair to a new channel pair if it is determined that the new channel pair reports better performance than the selected channel pair.

* * * * *